United States Patent
Machida (10) Patent No.: US 9,265,474 B2
(45) Date of Patent: Feb. 23, 2016

(54) IMAGE PROCESSING APPARATUS AND IMAGE PROCESSING METHOD

(71) Applicant: CANON KABUSHIKI KAISHA, Tokyo (JP)

(72) Inventor: Yoshihito Machida, Sagamihara (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 188 days.

(21) Appl. No.: 13/804,485

(22) Filed: Mar. 14, 2013

(65) Prior Publication Data
US 2013/0261443 A1    Oct. 3, 2013

(30) Foreign Application Priority Data
Mar. 27, 2012  (JP) ................. 2012-072342

(51) Int. Cl.
*G06K 9/00* (2006.01)
*A61B 6/00* (2006.01)

(52) U.S. Cl.
CPC ........... *A61B 6/5205* (2013.01); *A61B 6/481* (2013.01); *A61B 6/504* (2013.01)

(58) Field of Classification Search
None
See application file for complete search history.

(56) References Cited

U.S. PATENT DOCUMENTS

| | | | | |
|---|---|---|---|---|
| 4,907,156 A * | 3/1990 | Doi | ........... | G06T 5/004 382/130 |
| 5,224,177 A * | 6/1993 | Doi | ........... | G06T 5/007 382/168 |
| 5,268,967 A * | 12/1993 | Jang | ........... | G06T 7/0012 382/132 |
| 5,359,513 A * | 10/1994 | Kano | ........... | G06T 3/0081 128/922 |
| 5,361,763 A * | 11/1994 | Kao | ........... | G01R 33/56 382/145 |
| 5,743,266 A * | 4/1998 | Levene | ........... | A61B 8/06 600/458 |
| 5,892,840 A * | 4/1999 | Jang | ........... | G06T 7/0012 378/162 |
| 5,956,435 A * | 9/1999 | Buzug | ........... | G06K 9/6215 382/130 |
| 7,532,214 B2 * | 5/2009 | Lundstrom | ........... | G06T 15/08 345/424 |
| 7,756,324 B2 * | 7/2010 | Ohishi | ........... | A61B 6/481 345/419 |
| 8,090,171 B2 * | 1/2012 | Kramp | ........... | A61B 6/481 378/4 |
| 8,208,701 B2 * | 6/2012 | Lendl | ........... | A61B 6/12 382/128 |

(Continued)

FOREIGN PATENT DOCUMENTS

| | | |
|---|---|---|
| JP | 11-047123 | 2/1999 |
| JP | 2005295139 A * | 10/2005 |

*Primary Examiner* — Chan Park
*Assistant Examiner* — Iman K Kholdebarin
(74) *Attorney, Agent, or Firm* — Fitzpatrick, Cella, Harper & Scinto (57) ABSTRACT

A histogram of pixel values in a difference image between a post-injection X-ray image and composite image is generated. A histogram of pixel values in a difference image between a pre-injection X-ray image and the composite image is generated. From the difference between the histograms, information on pixel values in a region where a radiopaque dye is imaged in the difference image between the post-injection X-ray image and composite image is collected. Pixel values in the difference image between the post-injection X-ray image and composite image are converted by using the collected information, and the converted difference image is output.

13 Claims, 6 Drawing Sheets

(56) References Cited

U.S. PATENT DOCUMENTS

| | | | |
|---|---|---|---|
| 8,295,553 B2 | 10/2012 | Machida | 382/107 |
| 8,437,519 B2* | 5/2013 | Baumgart et al. | 382/128 |
| 2002/0151780 A1* | 10/2002 | Klotz | A61B 6/481 600/407 |
| 2002/0181754 A1* | 12/2002 | Masumoto | G06T 7/0081 382/131 |
| 2004/0081342 A1* | 4/2004 | Sato | G06T 5/50 382/128 |
| 2005/0111719 A1* | 5/2005 | Pescatore | G06T 3/0068 382/130 |
| 2005/0141747 A1* | 6/2005 | Shi | G06T 1/0028 382/100 |
| 2005/0157916 A1* | 7/2005 | Sato | G06T 5/50 382/130 |
| 2005/0267349 A1* | 12/2005 | Goto | G06F 19/321 600/407 |
| 2006/0132483 A1* | 6/2006 | Ohishi | A61B 6/481 345/419 |
| 2007/0036405 A1* | 2/2007 | Lienard | G06T 5/50 382/128 |
| 2007/0116332 A1* | 5/2007 | Cai | G06K 9/4609 382/128 |
| 2007/0248251 A1* | 10/2007 | Liao | G06K 9/00208 382/128 |
| 2008/0037845 A1* | 2/2008 | Deuerling-Zheng | G06T 7/0026 382/130 |
| 2008/0051648 A1* | 2/2008 | Suri | A61B 6/481 600/407 |
| 2008/0278596 A1* | 11/2008 | Machida | H04N 5/335 348/222.1 |
| 2009/0003519 A1* | 1/2009 | Defreitas | A61B 6/502 378/37 |
| 2009/0185024 A1* | 7/2009 | Fukamachi | G03G 15/0126 347/236 |
| 2009/0185730 A1* | 7/2009 | Baumgart | A61B 6/4441 382/130 |
| 2009/0213394 A1* | 8/2009 | Machida | H04N 1/40037 358/1.9 |
| 2010/0128942 A1* | 5/2010 | Licato | G06T 7/0014 382/128 |
| 2010/0254575 A1* | 10/2010 | Machida | G06T 7/2053 382/107 |
| 2010/0260386 A1* | 10/2010 | Machida | G06T 5/50 382/107 |
| 2011/0299749 A1* | 12/2011 | Rauch | G06T 7/2053 382/130 |
| 2012/0002083 A1* | 1/2012 | Machida | G06T 3/4038 348/239 |
| 2012/0049081 A1* | 3/2012 | Machida | H04N 7/181 250/393 |
| 2012/0201439 A1* | 8/2012 | Rauch | G06T 7/20 382/130 |
| 2012/0250974 A1* | 10/2012 | Miyamoto | A61B 6/481 382/132 |
| 2013/0094734 A1* | 4/2013 | Rauch | G06T 7/0038 382/130 |

\* cited by examiner

IMAGE PROCESSING APPARATUS AND IMAGE PROCESSING METHOD

BACKGROUND OF THE INVENTION

1. Field of the Invention

The present invention relates to an image processing technique for an X-ray image.

2. Description of the Related Art

There is a procedure called angiography for extracting a structure such as a blood vessel that cannot be seen by ordinary X-ray imaging. Angiography is an imaging method of extracting a blood vessel by injecting a medicine called a radiopaque dye into the blood vessel and performing X-ray imaging.

As this angiography, there is an image processing method called digital subtraction angiography (DSA) that extracts only a blood vessel by removing structures except for the blood vessel by performing a subtraction process between an image before a radiopaque dye is injected and an image after the radiopaque dye is injected.

A DSA image as an image obtained by this DSA has the problem that the subtraction process makes noise larger than that of an image before the subtraction. Japanese Patent Laid-Open No. 11-47123 has disclosed a technique that reduces noise by performing tone processing by which the contrast of a pixel value close to 0 decreases.

When reducing noise by this tone processing, it is necessary to give proper tone conversion characteristic data. If tone processing is performed so as to broaden a contrast decreasing range in order to increase the DSA image noise reducing effect, the contrast of even an angiography region sometimes decreases. On the contrary, if the contrast decreasing range is narrowed, it is sometimes impossible to obtain a sufficient noise reducing effect.

SUMMARY OF THE INVENTION

The present invention has been made in consideration of the above situation, and provides a technique for reducing noise of a DSA image, and increasing the extractability of an angiography region.

According to one aspect of the present invention, there is provided an image processing apparatus comprising: a generation unit configured to generate a histogram of a pixel value in a difference image between an X-ray image of a radiopaque dye injection target portion imaged after a radiopaque dye is injected and an X-ray image of the radiopaque dye injection target portion imaged before the radiopaque dye is injected; and a conversion unit configured to convert the pixel value in the difference image based on the histogram.

According to another aspect of the present invention, there is provided an image processing apparatus comprising: a first generation unit configured to generate a histogram of a pixel value in a difference image between an X-ray image of a radiopaque dye injection target portion imaged after a radiopaque dye is injected and an X-ray image of the radiopaque dye injection target portion imaged before the radiopaque dye is injected; a second generation unit configured to generate a histogram of a noise amount corresponding to a pixel value in the X-ray image of the radiopaque dye injection target portion imaged before the radiopaque dye is injected; and a conversion unit configured to convert the pixel value in the difference image, based on a difference between the histogram generated by the first generation unit and the histogram generated by the second generation unit.

According to still another aspect of the present invention, there is provided an image processing method comprising: a generation step of generating a histogram of a pixel value in a difference image between an X-ray image of a radiopaque dye injection target portion imaged after a radiopaque dye is injected and an X-ray image of the radiopaque dye injection target portion imaged before the radiopaque dye is injected; and a conversion step of converting the pixel value in the difference image based on the histogram.

According to yet another aspect of the present invention, there is provided an image processing method comprising: a first generation step of generating a histogram of a pixel value in a difference image between an X-ray image of a radiopaque dye injection target portion imaged after a radiopaque dye is injected and an X-ray image of the radiopaque dye injection target portion imaged before the radiopaque dye is injected; a second generation step of generating a histogram of a noise amount corresponding to a pixel value in the X-ray image of the radiopaque dye injection target portion imaged before the radiopaque dye is injected; and a conversion step of converting the pixel value in the difference image, based on a difference between the histogram generated in the first generation step and the histogram generated in the second generation step.

Further features of the present invention will become apparent from the following description of exemplary embodiments with reference to the attached drawings.

DESCRIPTION OF THE EMBODIMENTS

Embodiments of the present invention will be explained below with reference to the accompanying drawings. Note that each embodiment to be explained below is an example when the present invention is practiced, and is one practical example of configurations described in the scope of claims.

First Embodiment

Figure 1:
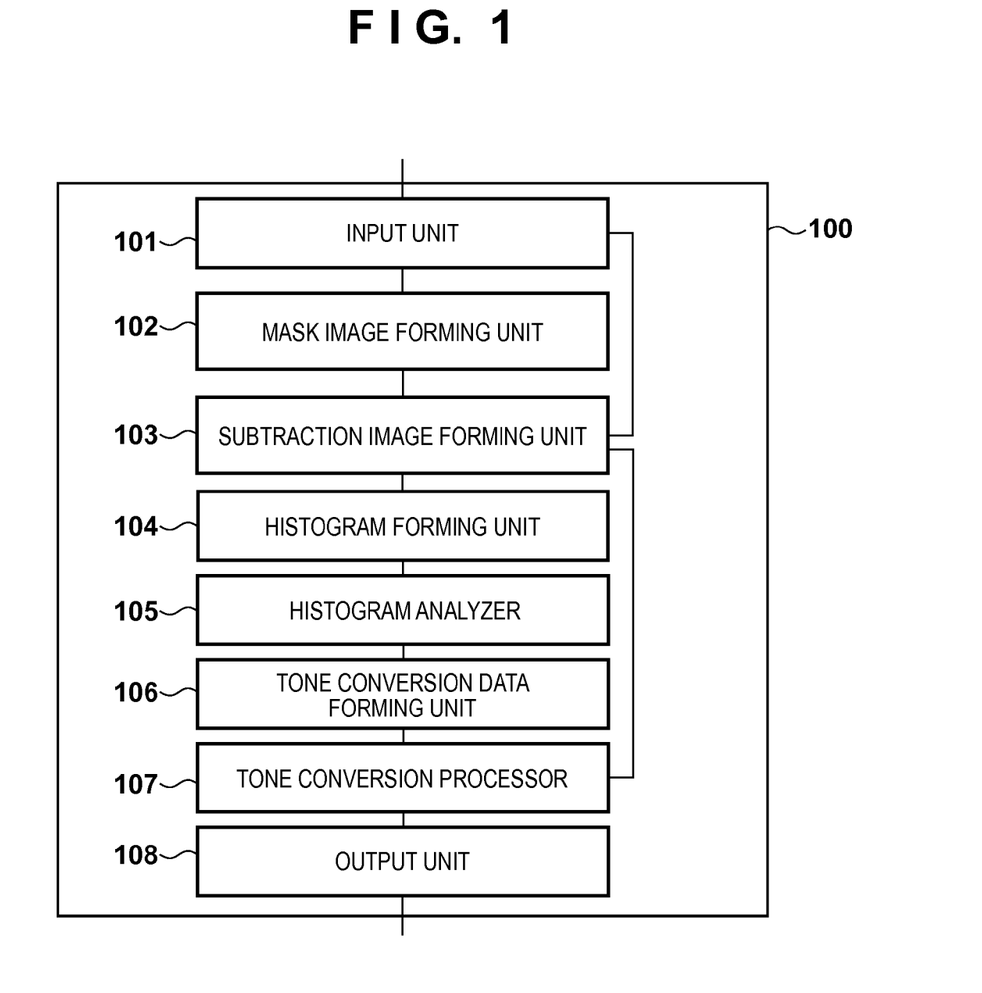
FIG. 1 is a block diagram showing an example of the functional configuration of an image processing apparatus.
Figure 2:
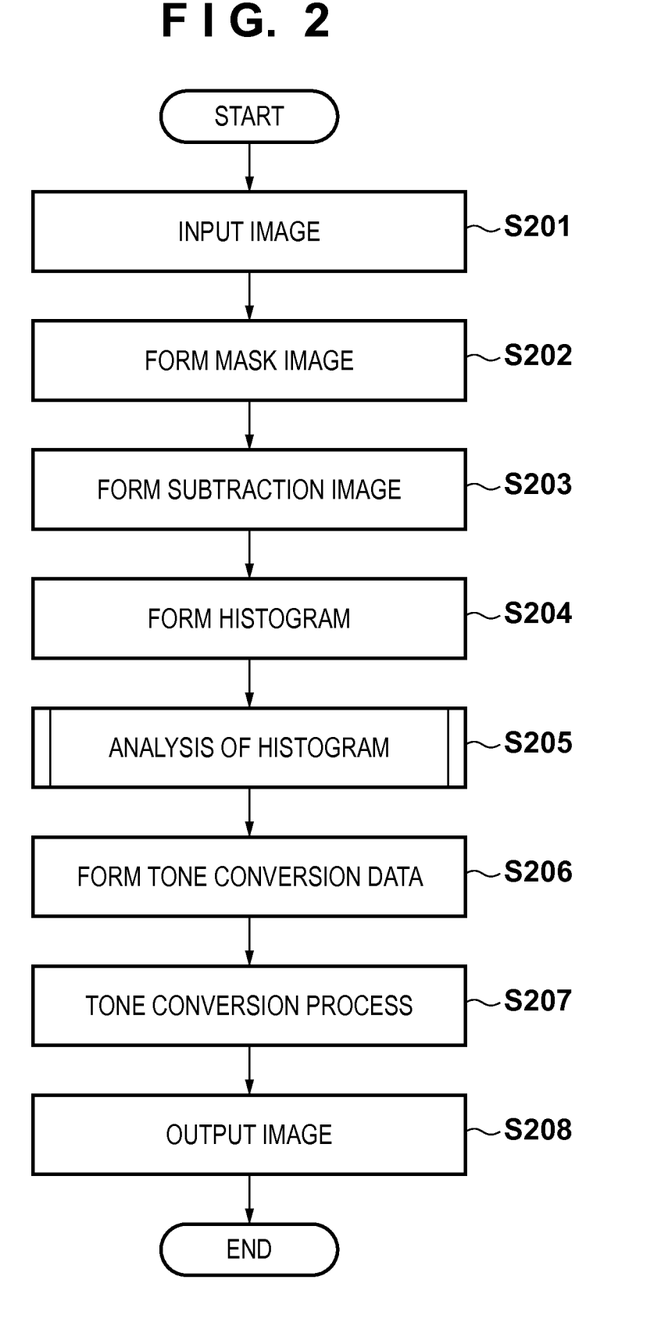
FIG. 2 is a flowchart of processing performed by the image processing apparatus.

FIG. 1 shows an example of the functional configuration of an image processing apparatus according to this embodiment. The operation of each unit shown in FIG. 1 will be explained with reference to FIG. 2 showing the flowchart of processing performed by the image processing apparatus.

In step S201, an input unit 101 receives, from an X-ray image supply apparatus, X-ray images obtained by continuously imaging a target portion into which a radiopaque dye is injected (a radiopaque dye injection target portion) from a state before the radiopaque dye is injected to a state after the radiopaque dye is injected. The X-ray image supply apparatus can be an X-ray radioscopy apparatus for capturing the X-ray images or an image storage device storing the X-ray images. However, the supply form of X-ray images is not limited to any specific supply form.

Then, the input unit 101 outputs some of sequentially input X-ray images to a mask image forming unit 102, and outputs the rest to a subtraction image forming unit 103. In this embodiment, X-ray images (pre-injection X-ray images) of a plurality of frames obtained before the radiopaque dye is injected are output to the mask image forming unit 102. Also, of the sequentially input X-ray images, an X-ray image of at least one frame obtained before the radiopaque dye is injected and an X-ray image (post-injection X-ray image) of each frame obtained after the radiopaque dye is injected are output to the subtraction image forming unit 103. In the following description, an X-ray image output from the input unit 101 to the subtraction image forming unit 103 will be called a live image.

In step S202, the mask image forming unit 102 synthesizes the X-ray images of the individual frames input from the input unit 101, thereby generating one composite image (mask image). The composite image generating method is not limited to any specific method, and it is possible to use, for example, the following method.

For example, the average pixel value of pixel values at the same position P in N (N is a natural number of 2 or more) X-ray images is calculated, and the calculated average pixel value is set as the pixel value of the pixel position P in the composite image (average image).

In another method, motion vectors are first calculated from N X-ray images. Then, an average pixel value is adopted for a portion where the motion is small (where the size of the motion vector is less than a predetermined value), and a pixel value obtained by reducing noise by using a spatial filter is adopted for a portion where the motion is large (where the size of the motion vector is equal to or larger than the predetermined value), thereby generating a composite image.

A mask image having little noise can be generated by the processing as described above. In step S202, it is only necessary to generate a mask image having little noise.

Subsequently, in step S203, the subtraction image forming unit 103 generates difference images (subtraction images) of the live images and composite image (first generation and second generation). As described above, the live images include a pre-injection X-ray image of at least one frame obtained before the radiopaque dye is injected, and a post-injection X-ray image obtained after the radiopaque dye is injected. Accordingly, the subtraction image forming unit 103 generates a difference image of the pre-injection X-ray image and composite image (an image obtained by subtracting the composite image from the pre-injection X-ray image), and a difference image of the post-injection X-ray image and composite image (an image obtained by subtracting the composite image from the post-injection X-ray image). The subtraction image forming unit 103 outputs the two generated difference images to a histogram forming unit 104 and tone conversion processor 107.

In step S204, the histogram forming unit 104 generates a pixel value histogram (the appearance frequencies of pixel values contained in a difference image) for each of the difference images received from the subtraction image forming unit 103. In the following description, the histogram of pixel values in the difference image of the pre-injection X-ray image and composite image will be called a noise histogram, and the histogram of pixel values in the difference image of the post-injection X-ray image and composite image will be called an angiography histogram. The histogram forming unit 104 outputs the two generated histograms to a histogram analyzer 105.

In step S205, the histogram analyzer 105 collects information (angiography region pixel value information) about pixel values of a region (angiography region) in which the radiopaque dye is captured in the difference image of the post-injection X-ray image and composite image, from the difference between the noise histogram and angiography histogram. The angiography region pixel value information to be collected can be predetermined in accordance with the purpose of later processing. The angiography region pixel value information contains, for example, a minimum pixel value, maximum pixel value, maximum frequency, intermediate value, and average value in the angiography region. The histogram analyzer 105 outputs the collected angiography region pixel value information to a tone conversion data forming unit 106. Details of the processing in step S205 will be described later.

In step S206, the tone conversion data forming unit 106 generates tone conversion data for converting an input pixel value into an output pixel value by using the angiography region pixel value information. When generating the tone conversion data, the angiography region pixel value information to be used can be changed in accordance with a target procedure or the like.

For example, when performing a procedure of extracting a wide range from a thin blood vessel having a low angiographic density to a thick blood vessel having a high angiographic density from the difference image of the post-injection X-ray image and composite image, the tone conversion data need only be formed such that the minimum and maximum pixel values in the angiography region pixel value information have desired values.

Also, when performing a procedure of extracting only the most conspicuous blood vessel from the difference image of the post-injection X-ray image and composite image, the tone conversion data need only be formed such that the maximum frequency value in the angiography region pixel value information has a desired value.

In addition, pixel values except for the angiography region belong to a noise region, so a noise reducing effect can be obtained by decreasing the contrast in this portion. It is thus possible to obtain the noise reducing effect and increase the extractability of the angiography region by using the angiography region pixel value information. The tone conversion data forming unit 106 outputs the tone conversion data generated as described above to the tone conversion processor 107.

In step S207, of the pixel values in the difference image of the post-injection X-ray image and composite image, the tone conversion processor 107 converts a pixel value defined as the pixel value of a conversion source by the tone conversion data into a pixel value defined as a conversion destination of the pixel value by the tone conversion data. Consequently, tone conversion can be performed on this difference image. The tone conversion processor 107 outputs the tone-converted difference image as a DSA image to an output unit 108.

In step S208, the output unit 108 outputs the DSA image to a display device such as a CRT or liquid crystal screen, thereby displaying the DSA image on the display device. The output destination of the DSA image is, of course, not limited to the display device, and may also be a hard disk or memory for saving the DSA image, or an image processing apparatus for performing a minimum value holding process or the like.

Figure 3:
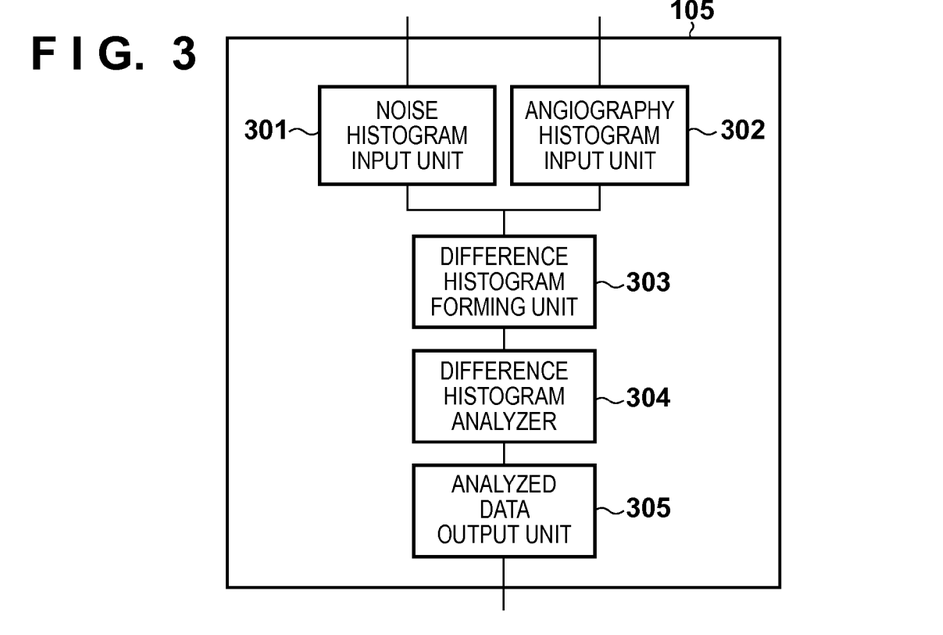
FIG. 3 is a block diagram showing an example of the functional configuration of a histogram analyzer 105.

Next, details of the processing in step S205 described above will be explained with reference to FIG. 4 showing the flowchart of the processing. Also, FIG. 3 is a block diagram showing an example of the functional configuration of the histogram analyzer 105. The operation of each unit shown in FIG. 3 will be explained with reference to FIG. 4.

Figure 4:
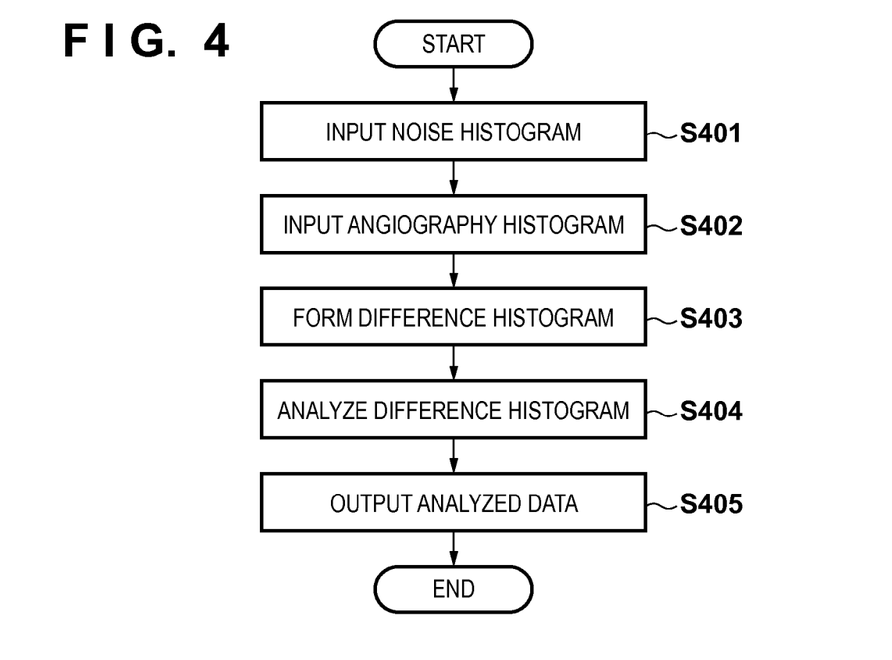
FIG. 4 is a flowchart of processing in step S205.

In step S401, a noise histogram input unit 301 receives the noise histogram, and outputs the input noise histogram to a difference histogram forming unit 303 in the output stage. Since no radiopaque dye is imaged in this noise histogram and the image is formed by only noise, the pixel value distribution of only noise can be analyzed.

In step S402, an angiography histogram input unit 302 receives the angiography histogram, and outputs the input angiography histogram to the difference histogram forming unit 303 in the output stage. Since the angiography histogram is an image in which the radiopaque dye is imaged, the pixel value distribution contains both noise and the radiopaque dye.

In step S403, the difference histogram forming unit 303 generates a difference histogram by subtracting the noise histogram from the angiography histogram. In this difference histogram generation, the result obtained by subtracting the frequency value of the pixel value P in the noise histogram from the frequency value of the pixel value P in the angiography histogram is set as the frequency value of the pixel value P in the difference histogram.

Figure 5A:
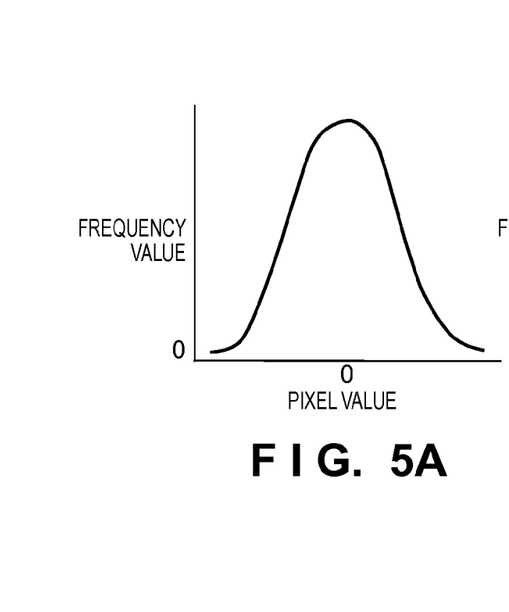
FIGS. 5A to 5C are views showing examples of histograms.
Figure 5B:
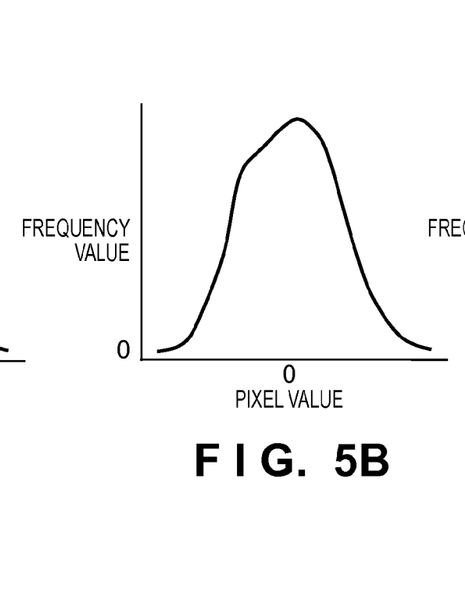
Figure 5C:
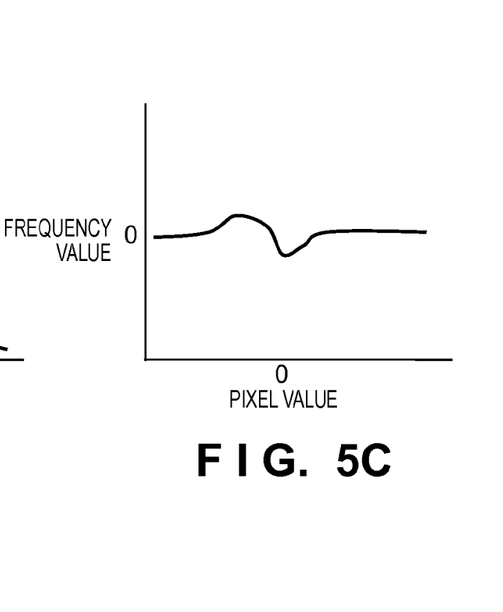

Since the difference histogram generated as described above is obtained by subtracting the histogram of the image containing only noise from the histogram of the image containing both noise and the radiopaque dye, a change in pixel distribution caused by the radiopaque dye can be known. FIG. 5A shows an example of the angiography histogram, FIG. 5B shows an example of the noise histogram, and FIG. 5C shows an example of the difference histogram. Since a peak portion of the difference histogram where the frequency value is 0 or more is formed by pixel values increased by the radiopaque dye, this portion is the angiography region. The difference histogram forming unit 303 outputs the generated difference histogram to a difference histogram analyzer 304 in the output stage.

Then, in step S404, the difference histogram analyzer 304 collects angiography region pixel value information from the difference histogram. As described above, pixels values in the angiography region form the peak portion of the difference histogram, it is only necessary to calculate, for example, the minimum pixel value, maximum pixel value, maximum frequency value, average value, and intermediate value of the peak portion. It is also possible to perform stable analysis unaffected by small variations in the histogram by collecting the angiography region pixel value information after performing a filtering process such as moving average. Furthermore, a clipping process can be performed on data having a frequency value of 0 or less because it is only necessary to detect a portion where the pixel value has increased. The difference histogram analyzer 304 outputs the collected angiography region pixel value information to an analyzed data output unit 305. Also, the definition of the peak portion is not limited to a frequency value of 0 or more, and may also be a portion occupied by frequency values equal to or larger than a predetermined value.

In step S405, the analyzed data output unit 305 outputs the angiography region pixel value information received from the difference histogram analyzer 304 to the tone conversion data forming unit 106.

By thus forming the histograms of the subtraction images before and after angiography, it is possible to obtain pixel value information of only the angiography region that cannot be extracted by subtraction between the subtraction images.

Modification 1

When the histogram analyzer 105 analyzes the difference histogram, the width of pixel values to be analyzed can also be limited in accordance with, for example, a target portion into which the radiopaque dye is injected, the amount of radiopaque dye to be used, the injection speed, the frame rate, and the imaging conditions. This makes it possible to increase the analytical accuracy.

Modification 2

The tone conversion data formed by the tone conversion data forming unit 106 can be generated for each frame, or tone conversion data generated for a given specific frame can be used for all frames. This makes it possible to form a DSA image having small contrast variations between frames.

Second Embodiment

Figure 6:
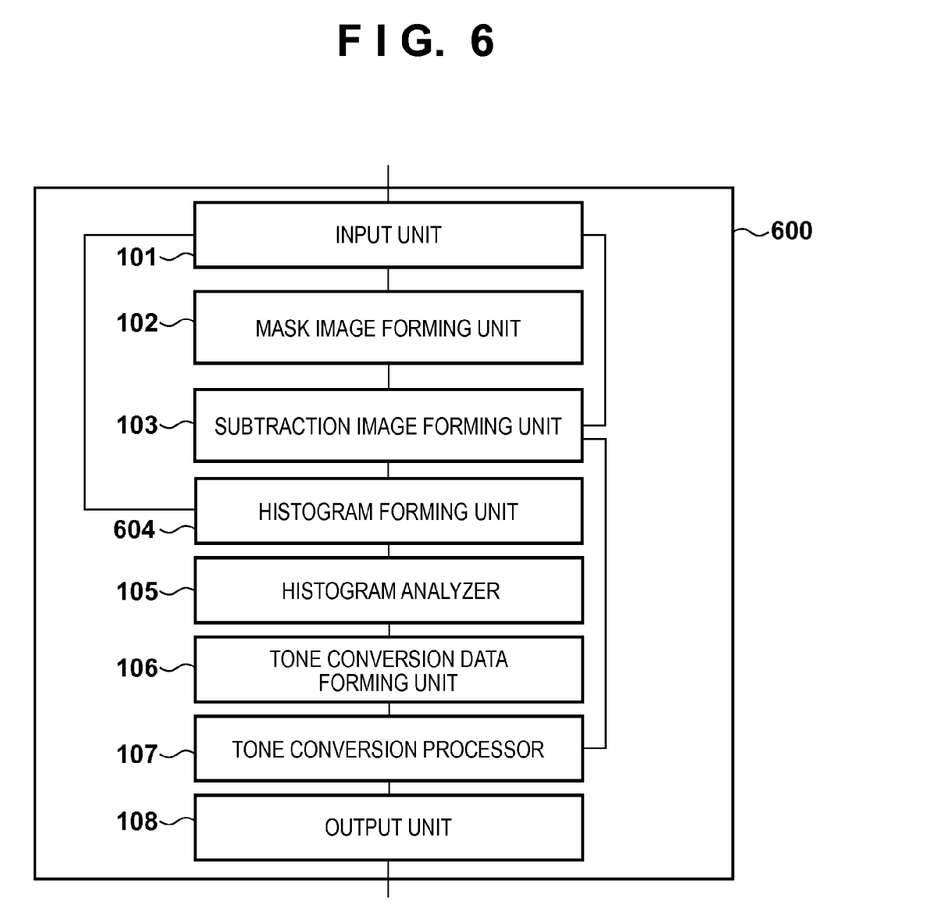
FIG. 6 is a block diagram showing an example of the functional configuration of an image processing apparatus.

This embodiment differs from the first embodiment in noise histogram formation method. FIG. 6 is a block diagram showing an example of the functional configuration of an image processing apparatus according to this embodiment. The same reference numerals as in FIG. 1 denote the same constituent elements in FIG. 6, and a repetitive explanation thereof will be omitted because these constituent elements have already been explained in the first embodiment.

A histogram forming unit 604 generates an angiography histogram and noise histogram. The angiography histogram is generated in the same manner as in the first embodiment. On the other hand, the noise histogram is generated as follows.

The noise histogram depends on the pixel value of a live image: as the X-ray dose and pixel value increase, the variance of X-ray quantum noise increases, and as a consequence the shape of the histogram spreads. The noise histogram also depends on the granularity of a mask image: when the granularity is improved by, for example, increasing the number of mask images to be averaged, the shape of the histogram narrows. To simplify the explanation, this embodiment will be explained by taking a state in which the number of mask images to be averaged is fixed as an example.

Figure 7:
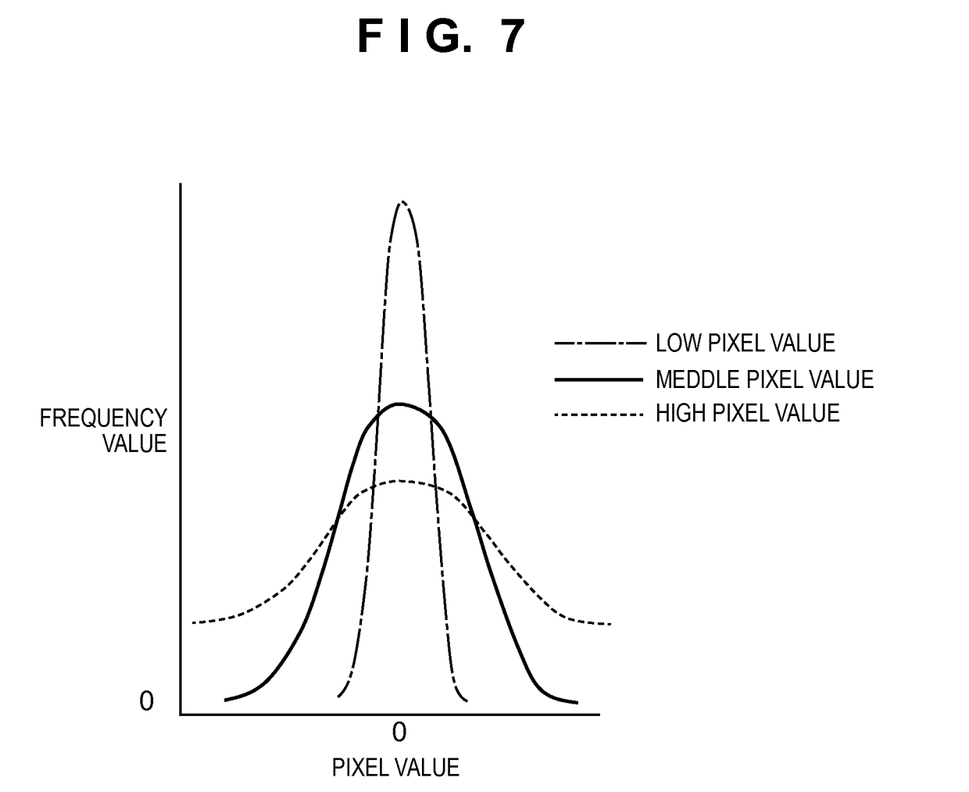
FIG. 7 is a view showing an example of noise data.

As described above, the noise histogram depends on the pixel value of a live image. Therefore, the noise histogram is formed by using noise data depending on the pixel value. FIG. 7 shows an example of the noise data. This noise data is obtained by dividing the frequency value by the number of pixels in a histogram formed by performing subtraction on an image generated by X-ray irradiation with a uniform dose on an entire surface by using a mask image formed by using an image obtained by uniform irradiation.

The noise histogram can be formed by integrating each pixel of a live image by referring to this noise data (that is, by adding the frequency value (noise amount) indicated for each pixel by the noise data to the frequency value of the pixel). By thus referring to the noise data from the live image, the noise histogram can be formed without performing any subtraction process on an image before angiography. Note that since the number of mask images to be averaged changes, noise data corresponding to each number of mask images to be averaged is used.

Note also that the noise data is not limited to premeasured data, and can also be data obtained by estimation from, for example, sensor system noise when an image is obtained, or a standard deviation of quantum noise depending on the pixel value of a live image and the number of mask images to be averaged. By thus estimating the noise data by an arithmetic operation, it is possible to form a noise histogram unaffected by an error caused by pixel value measurement or the like.

Third Embodiment

Each unit shown in FIGS. 1 and 6 can be configured by hardware, but can also be configured by software (a computer program). In this case, this software is installed on a computer including a CPU and memory, and the CPU is caused to execute the computer program. Consequently, the computer functions as an image processing apparatus explained in the first or second embodiment.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (for example, computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-072342 filed Mar. 27, 2012 which is hereby incorporated by reference herein in its entirety.

What is claimed is:

1. An image processing apparatus comprising:
a first generation unit configured to generate a first histogram of a DSA image, wherein the DSA image is a difference image between an X-ray image of a radiopaque dye injection target portion imaged after a radiopaque dye is injected and a mask image which is generated based on a pre-injection X-ray image of the radiopaque dye injection target portion imaged before the radiopaque dye is injected;
a second generation unit configured to generate a second histogram of a difference image between a first X-ray image of the radiopaque dye injection target portion which is imaged as a live image before the radiopaque dye is injected and a second image which is different from the first X-ray image and is generated based on the pre-injection X-ray image;
a determination unit configured to determine a pixel value, based on a difference between the first and second histograms; and
a conversion unit configured to convert pixel values in the DSA image based on the value determined by the determination unit.

2. The apparatus according to claim 1, wherein the first generation unit generates one composite image by synthesizing X-ray images of a plurality of frames of the radiopaque dye injection target portion imaged before the radiopaque dye is injected, and generates, as the first histogram, a histogram of a pixel value in a difference image between the generated composite image and the X-ray image of the radiopaque dye injection target portion imaged after the radiopaque dye is injected.

3. The apparatus according to claim 2, wherein the second generation unit generates, as the second histogram, a histogram of a pixel value in a difference image between the composited image and the X-ray image of the radiopaque dye injection target portion imaged before the radiopaque dye is injected,
wherein the conversion unit comprises a collection unit configured to collect information on a pixel value in a region, in the difference image, where the radiopaque dye is imaged, from a difference between the second histogram generated and the first histogram, and performs the conversion by using the collected information.

4. The apparatus according to claim 1, further comprising an output unit configured to output the converted DSA image.

5. The apparatus according to claim 3, wherein the collection unit generates a difference histogram by subtracting the second histogram from the first histogram, and collects information on a pixel value corresponding to a frequency value not less than a predetermined value in the difference histogram, as the information on the pixel value in the region where the radiopaque dye is imaged.

6. The apparatus according to claim 3, wherein when the collection unit collects a maximum pixel value and a minimum pixel value in the region where the radiopaque dye is imaged, the conversion unit converts the difference image between the composite image and the X-ray image of the radiopaque dye injection target portion imaged after the radiopaque dye is injected, such that the maximum pixel value and the minimum pixel value in the difference image are respectively predetermined values.

7. The apparatus according to claim 2, wherein the first generation unit calculates an average value of pixel values of pixels at identical positions in the X-ray images of the plurality of frames, as a pixel value of the corresponding position in the composite image.

8. The apparatus according to claim 5, wherein the collection unit performs a filtering process for the difference histogram to collect the information on a pixel value corresponding to a frequency value not less than a predetermined value in the difference histogram, as the information on the pixel value in the region where the radiopaque dye is imaged.

9. The apparatus according to claim 5, wherein the collection unit performs a clipping process for the difference histogram to collect the information on a pixel value corresponding to a frequency value not less than a predetermined value in the difference histogram, as the information on the pixel value in the region where the radiopaque dye is imaged.

10. The apparatus according to claim 1, wherein the second generation unit generates the second histogram of the difference image between the first X-ray image and a mask image which is different from the first X-ray image and is generated based on an X-ray image of the radiopaque dye injection target portion being imaged before the radiopaque dye is injected.

11. An image processing method comprising:
generating a first histogram of a DSA image, wherein the DSA image is a difference image between an X-ray image of a radiopaque dye injection target portion imaged after a radiopaque dye is injected and a mask image which is generated based on a pre-injection X-ray image of the radiopaque dye injection target portion imaged before the radiopaque dye is injected;

generating a second histogram of a difference image between a first X-ray image of the radiopaque dye injection target portion which is imaged as a live image before the radiopaque dye is injected and a second image which is different from the first X-ray image and is generated based on the pre-infection X-ray image;

determining a pixel value, based on a difference between the first and second histograms; and converting pixel values in the DSA image based on the pixel value determined in the step of determining.

12. A non-transitory computer-readable storage medium storing a computer program for causing a computer to function as;

a first generation unit configured to generate a first histogram of a DSA image, wherein the DSA image is a difference image between an X-ray image of a radiopaque dye injection target portion imaged after a radiopaque dye is injected and a mask image which is generated based on a pre-injection X-ray image of the radiopaque dye injection target portion imaged before the radiopaque dye is injected;

a second generation unit configured to generate a second histogram of a difference image between a first X-ray image of the radiopaque dye injection target portion which is imaged as a live image before the radiopaque dye is injected and a second image which is different from the first X-ray image and is generated based on the pre-injection X-ray image;

a determination unit configured to determine a pixel value, based on a difference between the first and second histograms; and a conversion unit configured to convert pixel values in the DSA image based on the value determined by the determination unit.

13. An image processing apparatus comprising:

at least one processor and memory storing a program, operatively coupled to serve as:

a first generation unit configured to generate a first histogram of a DSA image, wherein the DSA image is a difference image between an X-ray image of a radiopaque dye injection target portion imaged after a radiopaque dye is injected and a mask image which is generated based on a pre-injection X-ray image of the radiopaque dye injection target portion imaged before the radiopaque dye is injected;

a second generation unit configured to generate a second histogram of a difference image between a first X-ray image of the radiopaque dye injection target portion which is imaged as a live image before the radiopaque dye is injected and a second image which is different from the first X-ray image and is generated based on the pre-injection X-ray image;

a determination unit configured to determine a value, based on a difference between the first and second histograms; and a conversion unit configured to convert pixel values in the DSA image based on the value determined by the determination unit.

* * * * *